(12) United States Patent
Pettit et al.

(10) Patent No.: US 6,686,445 B1
(45) Date of Patent: Feb. 3, 2004

(54) SYNTHETIC ANTINEOPLASTIC AGENTS DERIVED FROM DOLASTATIN 15 AND METHODS OF MAKING SAME

(75) Inventors: George R. Pettit, Paradise Valley, AZ (US); Erik J. Flahive, Tempe, AZ (US)

(73) Assignee: Arizona Board of Regents, acting for and on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 09/509,066

(22) PCT Filed: Sep. 23, 1998

(86) PCT No.: PCT/US98/19954

§ 371 (c)(1), (2), (4) Date: Mar. 21, 2000

(87) PCT Pub. No.: WO99/15130

PCT Pub. Date: Apr. 1, 1999

Related U.S. Application Data

(60) Provisional application No. 60/059,853, filed on Sep. 24, 1997.

(51) Int. Cl.⁷ .................................................. C07K 7/00
(52) U.S. Cl. ...................... 530/330; 530/333; 530/338; 514/17
(58) Field of Search ............................ 514/17; 530/330, 530/333, 338

(56) References Cited

U.S. PATENT DOCUMENTS

| | | | |
|---|---|---|---|
| 5,654,399 A | 8/1997 | Sakakibara et al. | 530/330 |
| 5,663,149 A | 9/1997 | Pettit et al. | 514/17 |
| 5,780,588 A | 7/1998 | Pettit et al. | 530/330 |

FOREIGN PATENT DOCUMENTS

| WO | WO 93/23424 A | 11/1993 |
|---|---|---|
| WO | WO 97/17364 A | 5/1997 |

Primary Examiner—Christopher S. F. Low
Assistant Examiner—David Lukton
(74) Attorney, Agent, or Firm—Richard R. Mybeck; Susan Stone Rosenfield

(57) ABSTRACT

A composition of matter, denominated herein as 12a–r, having the structural formula set forth below:

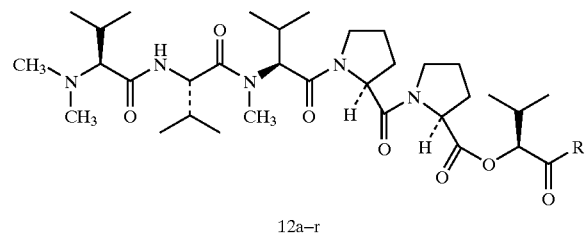

12a–r wherein R is selected from the group consisting of:
a) R=NHPh;
b) R=NHCH$_2$Ph;
c) R=NH(CH$_2$)$_2$Ph;
d) R=NH(CH$_2$)$_2$-4-F-Ph;
e) R=NH(CH$_2$)$_2$-4-Cl-Ph;
f) R=NH(CH$_2$)$_2$-3-Cl-Ph;
g) R=NH(CH$_2$)$_2$-2-Cl-Ph;
h) R=NH(CH$_2$)$_2$-4-Br-Ph;
i) R=NH(CH$_2$)$_2$-4-NO$_2$-Ph;
j) R=NH(CH$_2$)$_2$-3,4-(CH$_3$O)$_2$Ph;
k) R=NH(CH$_2$)$_2$-2-pyridine;
l) R=NH(CH$_2$)$_3$Ph;
m) R=L-Phe-OCH$_3$;
n) R=L-Met-OCH$_3$;
o) R=L-Pro-OCH$_3$;
p) R=NH-2-thiazolyl;
q) R=NH-2-benzothiazolyl;
r) R=NH-3-quinolyl;
and methods of making these compounds 12a–r.

22 Claims, No Drawings

SYNTHETIC ANTINEOPLASTIC AGENTS DERIVED FROM DOLASTATIN 15 AND METHODS OF MAKING SAME

This Application is based on U.S. Provisional Applications S/No. 60/059,853, filed Sep. 24, 1997, and is the national phase of PCT Ser. No. PCT/US98/19954, filed Sep. 23, 1998, which was assigned International Publication Number WO 99/15130.

Dolastatin 15, a known and potent antineoplastic constituent of the Indian Ocean shell-less mollusk *Dolabella auricularia*, was utilized as the lead substance from which were developed a series of novel derivatives. The present invention relates to methods of synthetically producing these new agents and presents their in vitro evaluations against a variety of murine and human cancer cell lines, and against a selection of bacteria and fungi. The effect of these derivatives on the inhibition of tubulin polymerization is also disclosed. Surprisingly, all of the new compounds, in which the C-terminal (S)-dolapyrrolidinone unit (Dpy, 5) of Dolastatin 15 is replaced with a series of structurally diverse, more readily available and less expensive amides, show cancer cell growth inhibition activities which are quite comparable to those of Dolastatin 15 (see: U.S. Pat. No. 4,879,278, Pettit et al.) All of the new compounds were, however, less potent than Dolastatin 15 as inhibitors of tubulin polymerization. The structurally modified peptides also caused mitotic arrest in cultured cells and inhibited the growth of a Gram-negative bacterium.

Some of this work was funded by Outstanding Investigator Grant CA-44344-01-08 awarded by the Division of Cancer Treatment, National Cancer Institute, DHHS. The United States government may have certain rights to this invention.

Marine organisms are an exceptionally productive source of biologically active and medicinally important substances bearing unique structures (see: FAULKNER, D. J. 1994, Marine Natural Products, *Natural Products Reports*, 11, 355; KOBAYASHI, M., et al. 1994, Bioactive substances isolated from marine sponge, a miniature conglomerate of various organisms, *Pure and Applied Chemistry*, 819; and, KÖNIG, G. et al. 1994, Biological activities of selected marine natural products, *Planta Medica*, 60, 532–537). Illustrative are the Indian Ocean (see: PETTIT et al. 1993, The isolation of dolastatins 10–15 from the marine mollusk *Dolabella auricularia, Tetrahedron*, 49, 9151) and Japanese (see: NAKAMURA et al., 1995, Stereochemistry and total synthesis of Dolastatin E. *Tetrahedron Letters*, 36, 5059, and the references cited therein) varieties of the sea hare *Dolabella auricularia*, from which a large number of antineoplastic and/or cytostatic linear and cyclic peptides, designated the dolastatins, have been isolated. Most of these potentially important peptides contain unprecedented amino acid units. Among these, the linear peptides, dolastatin 15 (1) (see: PETTIT et al., 1989a, Isolation and structure of the cytostatic linear depsipeptide dolastatin 15, *Journal of Organic Chemistry*, 54, 6005) and dolastatin 10 (2) (see: PETTIT et al., 1987, The isolation and structure of a remarkable marine animal antineoplastic constituent: Dolastatin 10, *Journal of the American Chemical Society*, 109, 6883) have exhibited the most potent antineoplastic activity (see: U.S. Pat. Nos. 4,816,444; 4,879,278; 4,978,744 and 5,554,725; and Hu et al., 1993, Effects of dolastatins on human B-lymphocytic leukemia cell lines, *Leukemia Research*, 17, 333) and have been selected for clinical development. Indeed, Phase 1 clinical trials of dolastatin 10 (2) have been ongoing under the auspices of the U.S. National Cancer Institute since November, 1995.

Since 1984, considerable research efforts have been directed to exploring structural modifications of dolastatin 10 (2) (PETTIT et al., 1995, Antineoplastic Agents 337, Synthesis of Dolastatin 10 Structural Modifications, *Anticancer Drug Design*, 10, 529) and dolastatin 15 (1) for the purpose of developing new potential anticancer drugs. A number of structural modifications of these peptides have been investigated in order to alter the antineoplastic activity of the parent molecule and eliminate from each peptide where possible, the more synthetically challenging units, especially the phenylalanine-derived C-terminal segments. Preliminary structure/activity studies based on dolastatin 10 (2) suggested that the thiazole-containing C-terminal unit could be adequately replaced with β-phenethylamine without significant loss of activity, whereas certain other modifications led to moderate or more drastic loss of antiproliferative activity (see: PETTIT et al., 1995, Antineoplastic Agents 337, Synthesis of Dolastatin 10 Structural Modifications, *Anticancer Drug Design*, 10, 529) without significant change in inhibitory effects on tubulin assembly. In the case at hand, a series of structural modifications of dolastatin 15 were made in which the C-terminal dolapyrrolidinone unit (5) was replaced by various amides. In contrast to dolastatin 10, major structural changes in the C-terminal amide unit of dolastatin 15 had essentially no adverse affect upon the inhibitory effects of the depsipeptide against tumor cell growth, but did result in a moderate reduction in the inhibition of tubulin polymerization.

One major factor driving the present research arises from the inescapable fact that there is not enough *Dolabella auricularia* in the world to allow sufficient quantities of effective components to be isolated therefrom to meet the need of the cancer-afflicted population in a commercially feasible manner. Therefore, a commercially effective synthesis must be developed which is capable of replicating a molecule containing only those substituents which are effective to control or arrest or mitigate the spread of cancer cells through a human system inflicted therewith. It is toward that goal that the present invention is directed.

Materials and Methods

All amino acids (S-configurations) and derivatives which are discussed herein were used as obtained from Sigma-Aldrich Co. Other reagents (DEPC, DCC, EDC-HCl, HOBt, NMM, Et$_3$N, 4-pyrrolidinopyridine, TFA, etc. {Abbreviations used: DEPC (diethylphosphorocyanidate), DCC (N,N'-dicyclo-hexylcarbodiimide), EDC-HCl (1-ethyl-3-(3-dimethylaminopropyl)carbodiimide hydrochloride), WRK (Woodward's reagent K, 2-ethylphenylisoxazolium-3'-sulfonate), BroP (tris(dimethylamino) phosphonium bromide hexafluorophosphate), HOBt (1-hydroxybenzotriazole), NMM (4-methylmorpholine), Et$_3$N (triethylamine), TFA (trifluoroacetic acid), THF (tetrahydrofuran), EtOAc (ethyl acetate), AcOH (acetic acid), Z (benzyloxycarbonyl), Boc (tert-butyloxycarbonyl)}) described were also obtained from Sigma-Aldrich and used without further purification. Amines 6a–r were either redistilled or recrystallized. All solvents were redistilled, and solvent extracts of aqueous solutions were dried over anhydrous magnesium sulfate or sodium sulfate. THF was distilled from LiAlH$_4$. Reactions were monitored by thin-layer chromatography using ANALTECH silica gel GF (0.25 mm) plates visualized by either UV irradiation or 3% ceric sulfate in 3 N H$_2$SO$_4$ solution as appropriate. Crude products were purified by flash chromatography over silica gel (E. Merck, DARMSTADT, 70–230 mesh). The final peptide products (12a–r) were further purified by rapid gel permeation chromatography in methanol on a column of lipophilic SEPHADEX LH-20.

Melting points were measured with an ELECTROTHERMAL digital melting point apparatus, model IA9200, and are uncorrected. Optical rotation measurements were recorded on a PERKIN-ELMER 241 polarimeter in methanol (unless otherwise noted) at 25° C. IR spectra were obtained using a NICOLET FTIR Model MX-1 instrument. All $^1$H-NMR spectra were observed on a VARIAN GEMINI 300 MHz instrument with $CDCl_3$ or DMSO-$d_6$ as solvent as noted. The $^{13}$C-NMR spectra were obtained with a UNITY 500 MHz instrument in $CDCl_3$. EIMS data were recorded with a MAT 312 mass spectrometer. Elemental analyses were determined by Galbraith Laboratories, Inc. located in Knoxville, Tenn.

All compounds synthesized were first evaluated for in vitro antitumor activity against murine P388 lymphocytic leukemia cells and against murine L1210 leukemia cells and human CA46 Burkitt lymphoma cells using techniques described by Hamel & Lin (see: HAMEL, E., and LIN, C. M., 1993, Interaction of combretastatin, a new plant-derived antimitotic agent, with tubulin, *Biochemical Pharmacology*, 32, 3864). The compounds were also evaluated in the NCI's human tumor 60-cell-line in intro primary screen as described by Monks et al. (see: MONKS, A., SCUDIERO, et al., 1991, New colorimetric cytotoxicity assay for anticancer drug screening, *Journal of the National Cancer Institute*, 83, 757). Data analyses were performed using methods described by Boyd and Paull (see: BOYD, M. R., et al., 1995, Some practical considerations and applications of the National Cancer Institute in vitro anticancer drug discovery screen, *Drug Development Research*, 34, 91). A tubulin polymerization inhibition assay was performed according to a modified version of the procedure used previously and described by Muzaffar et al. (see: MUZAFFAR, A., et al., 1990, Antitubulin effects of derivatives of 3-demethylthiocolchicine, methylthio esters of natural colchicinoids, and thioketones derived from thiocolchicine, Comparison with colchicine, *Journal of Medicinal Chemistry*, 33, 567) to evaluate the effects of dolastatin 15 on cellular microtubule assembly. The new assay for these compounds employed a drug-tubulin preincubation (15 min.) with 10 $\mu$M tubulin in 0.8 M glutamate at 30° C., followed by addition of GTP and incubation (20 min.) at 30° C., with tubulin polymerization monitored turbidimetrically in GILFORD recording spectrophotometers.

Antimicrobial disk susceptibility tests were performed according to the method established by the National Committee for Clinical Laboratory Standards (NCCLS, 1997). MUELLER-HINTON agar was used for susceptibility testing of *Staphylococcus aureus*, *Enterococcus faecalis*, *Micrococcus luteus*, *Escherichia coli*, *Enterobacter cloacae*, *Bacillus subtilis*, *Pseudomonas aeruginosa*, and *Erwinia carotovora*, Gonococcal Typing agar for *Neisseria gonorrhoeae*, and YM agar for *Candida albicans* and *Cryptococcus neoformans*. Immediately prior to susceptibility assays, compounds were reconstituted in sterile DMSO and twofold dilutions applied to sterile 6-mm disks. Zones of inhibition were read at 16 hours for bacterial cultures (except for *M. luteus*) and 42 hours for fungal cultures and *M. luteus*. MIC determinations were performed in duplicate.

General Procedure for Synthesis of α-Hydroxy Amides 7a–r

Method A (Amides 7b–o)

N-(2-Phenyl)ethyl-(2S)-2-hydroxyisovaleramide (7c). To a stirred and cooled (0° C.) solution of (S)-(+)-Hiva (3, 2.0 g, 16.9 mmol), freshly redistilled 2-phenylethylamine (6c, 2.10 mL, 16.9 mmol), and NMM (1.86 mL, 16.9 mmol) in 30 mL dry $CH_2Cl_2$ is added DEPC (2.56 mL, 16.9 mmol) dropwise. The mixture is then allowed to reach room temperature over 2 hours and continuously stirred under Ar. The solution is washed with equal volumes of distilled $H_2O$ (three times) and dried, and the solvent is removed in vacuo to give a yellow oil which crystallized. The product is recrystallized (three times) from toluene-hexane to give analytically pure amide 7c as colorless needles (2.14 g, 58%). mp 100.2–100.5° C.; $R_f$ 0.28 (hexane-acetone, 2:1); $[\alpha]^{24}_D$ −42.0° (c=1.0); MS m/z (relative intensity) 221 (48, M$^+$), 168 (12), 148 (11), 130 (19), 104 (100), 91 (25), 73 (21), 55 (17); $^1$H NMR (300 MHz, $CDCl_3$) δ 0.81 (d, J=7.0 Hz, 3H, Val $CH_3$), 1.00 (d, J=7.1 Hz, 3H, Val $CH_3$), 2.11 [spd (septet of doublets), $J_1$=7.0 Hz, $J_2$=3.3 Hz, 1H, Hiva $CH_\beta$], 2.49 (bs, 1H, —OH), 2.84 (t, J=7.1 Hz, 2H, Ph-$CH_2$), 3.58 (m, J=6.8 Hz, 2H, N—$CH_2$), 3.94 (d, J=3.3 Hz, 1H, Hiva $CH_\alpha$), 6.42 (bs, 1H, NH), 7.20–7.34 (m, 5H, ArH). Anal. Calcd for $C_{13}H_{19}NO_2$: C, 70.56; H, 8.65; N, 6.33. Found: C, 70.89; H, 9.01; N, 6.17.

Method B (amides 7a, 7p–r)

N-(2-Benzothiazolyl)-(2S)-2-hydroxyisovaleramide (7q). A solution of (S)-(+)-Hiva (3, 1.00 g, 8.5 mmol), 2-aminobenzothiazole (6q, 1.27 g, 8.5 mmol) and HOBt (2.29 g, 17 mmol, 2 eq) in dry THF (15 ml) is cooled to 0° C., under $N_2$, with stirring. To the solution is added NMM (0.93 mL, 8.5 mmol) and a solution of DCC (1.75 g, 8.5 mmol) in THF (5 mL). The reaction is then allowed to reach room temperature over 2 hours. The solution is filtered and concentrated to dryness. The oily residue is dissolved in $CH_2Cl_2$ (50 mL) and washed successively with saturated $NaHCO_3$ solution (50 mL), $H_2O$ (50 mL), 10% citric acid solution (50 mL), and $H_2O$ (2×50 mL). The organic extract is then dried and the solvent evaporated under reduced pressure to give a crude white solid. Urea by-product is removed by repeated precipitations from ice-cold EtOAc, and the product is recrystallized (three times) from acetone-heptane to give the pure amide as colorless microcrystalline needles (1.8 g, 85%). mp 184.1–184.2° C.; $R_f$ 0.59 ($CH_2Cl_2$-EtOAc, 4:1); $[\alpha]^{24}_D$ −69.3° (c=1.0); MS m/z 250 (9, M$^+$), 151 (14), 150 (100), 123 (8), 96 (7), 82 (21), 80 (21), 73 (6), 55 (13); $^1$H NMR (300 MHz, $CDCl_3$) δ 0.97 (d, J=6.9 Hz, 3H, Val $CH_3$), 1.23 (d, J=6.9 Hz, 3H, Val $CH_3$), 2.45 (spd, $J_1$=6.9 Hz, $J_2$=3.0 Hz, 1H, Hiva $CH_\beta$), 4.41 (bt, J=3.0 Hz, 1H, Hiva $CH_\alpha$), 5.00 (bd, J=3.9 Hz, 1H, OH), 7.35 (t, J=8.4 Hz, 1H, ArH), 7.47 (t, J=8.4 Hz, 1H, ArH), 7.76 (d, J=8.4 Hz, 1H, ArH), 7.85 (d, J=7.5 Hz, 1H, ArH), 10.55 (bs, 1H, NH). Anal. Calcd. For $C_{12}H_{14}N_2O_2S$: C, 57.78; H, 5.64; N, 11.9. Found: C, 57.90; H, 5.87; N, 10.89.

For the physical properties of amides 7a–r, see Table I, below.

TABLE I

Physical constants for α-hydroxy amides 7a–r.

| Compound | % yield[a] | $R_f$[b] | mp (° C.) | $[\alpha]_D^{25}$[e] | MS |
|---|---|---|---|---|---|
| 7a | 98 | 0.46 | 85.5 | −82.3° | 193 (M+), 151, 121, 94, 93, 77, 73, 66, 55 |
| 7b | 57 | 0.46[c] | 90.0–90.1 | −37.5° | 207 (M+), 189, 175, 165, 135, 106, 91, 73, 65, 55 |
| 7c | 58 | 0.28 | 100.2–100.5 | −42.0° | 221 (M+), 168, 148, 130, 104, 91, 73, 55 |
| 7d | 42 | 0.31 | 100.1–100.3 | −37.1° | 239 (M+), 196, 166, 130, 123, 122, 109, 83, 73, 55 |
| 7e | 54 | 0.32 | 113.9–114.0 | −37.0° | 255 (M+), 212, 196, 182, 140, 138, 130, 89, 73, 55 |
| 7f | 88 | 0.33[c] | 87.9–88.0 | −33.1° | 255 (M+), 212, 182, 140, 139, 138, 130, 126, 103, 88, 77, 73, 55 |
| 7g | 55 | 0.39[c] | 54.9–55.0 | −47.3° | 255 (M+), 220, 214, 196, 182, 138, 137, 130, 89, 73, 55 |
| 7h | 72 | 0.32 | 125.0–125.3 | −37.0° | 301 (M+), 299, 258, 184, 182, 169, 135, 130, 104, 90, 73, 55 |
| 7i | 45 | 0.25 | 111.8–112.0 | −37.9° | 266 (M+), 223, 194, 177, 150, 137, 133, 121, 103, 91, 73, 55 |
| 7j | 81 | 0.19 | 104.5–104.7 | −27.5° | 281 (M+), 164, 151, 137, 121, 107, 91, 73, 55 |
| 7k | 53 | 0.49[d] | 102.5 | −37.2° | 222 (M+), 179, 149, 121, 106, 93, 78, 66, 51 |
| 7l | 80 | 0.31 | 61.0–61.4 | −35.6° | 235 (M+), 192, 162, 313, 118, 117, 113, 91, 83, 73, 55 |
| 7m | 59 | 0.41[c] | 73.2 | −23.9° | 279 (M+), 236, 220, 176, 162, 146, 131, 120, 91, 88, 73, 55 |
| 7n | 70 | 0.35[c] | 40.0–40.5 | −38.3° | 263 (M+), 202, 189, 171, 157, 139, 104, 89, 73, 61, 56, 55 |
| 7o | 21[f] | 0.37 | | | |
| 7p | 57 | 0.28 | oil | −54.5° | 200 (M+), 127, 102, 101, 100, 76, 73, 58, 55 |
| 7q | 85 | 0.59[c] | 184.1–184.2 | −69.3° | 250 (M+), 151, 150, 123, 96, 82, 80, 73, 55 |
| 7r | 46 | 0.39[c] | 198.0–198.2 | −99.0° | 244 (M+), 173, 144, 128, 117, 89, 73, 55 |

[a]Yields are for the pure isolated product after chromatography and/or recrystallization.
[b]2:1 hexane:acetone
[c]4:1 $CH_2Cl_2$—EtOAc
[d]9:1 $CH_2Cl_2$—$CH_3OH$
[e]c = 1.0, $CH_3OH$
[f]The yield of 7o was low due to spontaneous diketomorpholine formation under the reaction conditions; the product was carried through to the subsequent step without characterization.

General Procedure for Synthesis of Boc-Depsipeptides 8a–r
N-[(2S)-O-[N-(tert-Butyloxycarbonyl)prolyl]-2-hydroxyisovaleryl]-2-phenylethylamide (8c). A solution of amide 7c (0.50 g, 2.26 mmol) in $CH_2Cl_2$ (2 mL) is added slowly to a dry, stirred solution of t-Boc-S-proline (0.58 g, 2.71 mmol, 1.2 eq), 4-pyrrolidinopyridine (0.335 g, 2.71 mmol, 1.2 eq), and DCC (0.56 g, 2.71 mmol, 1.2 eq) in $CH_2Cl_2$. The solution is stirred for 20 hours at room temperature under Ar, filtered, and concentrated under reduced pressure to give an oil. The oily residue is then chromatographed on silica gel (25% acetone-hexane) to afford 0.95 g (100%) of ester 8c as a colorless gum (after drying in vacuo). $R_f$ 0.52 (hexane-acetone, 2:1); $[\alpha]_D^{25}$−63.5° (c=0.2); MS m/z 418 (16, M+), 362 (8), 327 (8), 271 (15), 170 (6), 142 (29), 114 (66), 105 (30), 91 (6), 70 (100), 57 (54); $^1H$ NMR (300 MHz, $CDCl_3$) δ 0.87 (d, J=6.9 Hz, 3H, Val $CH_3$), 0.95 (d, J=6.9 Hz, 3H, Val $CH_3$), 1.48 (s, 9H, t-butyl), 1.82–2.00 (m, 2H, Pro $CH_2$), 2.05–2.14 (m, 1H, ½ Pro $CH_2$), 2.22–2.31 (m, 1H, ½ Pro $CH_2$), 2.44 (spd, $J_1$=6.9 Hz, $J_2$=2.7 Hz, 1H, Hiva $CH_\beta$), 2.87 (t, J=7.2 Hz, 2H, Ph-$CH_2$), 3.34–3.61 (m, 4H, Pro $CH_2$, N—$CH_2$), 4.39 (dd, $J_1$=8.7 Hz, $J_2$=4.2 Hz, 1H, Pro $CH_\alpha$), 5.07 (d, J=2.7 Hz, 1H, Hiva $CH_\alpha$), 7.16–7.32 (m, 5H, ArH), 7.66 (bs, 1H, NH).

For the physical properties of compounds 8a–r, see Table II.

TABLE II

Physical constants for depsidipeptide derivatives 8a–r.

| Compound | % yield[a] | $R_f$[b] | $[\alpha]_D^{25}$[d] | MS |
|---|---|---|---|---|
| 8a | 81 | 0.49 | −65.5° | 390 (M+), 334, 289, 177, 162, 142, 114, 93, 70, 57 |
| 8b | 92 | 0.51 | −41.5° | 404 (M+), 348, 189, 176, 170, 162, 114, 91, 70, 57 |
| 8c | 100 | 0.52 | −63.5° | 418 (M+), 362, 327, 271, 170, 142, 114, 105, 91, 70, 57 |

TABLE II-continued

Physical constants for depsidipeptide derivatives 8a–r.

| Compound | % yield[a] | $R_f$[b] | $[\alpha]_D^{25}$[d] | MS |
|---|---|---|---|---|
| 8d | 94 | 0.47 | −62.5° | 436 (M⁺), 380, 336, 271, 242, 170, 142, 115, 70, 57 |
| 8e | 93 | 0.71[c] | −82.5° | 452 (M⁺), 396, 352, 271, 242, 170, 142, 138, 114, 70, 57 |
| 8f | 94 | 0.44 | −58.5° | 452 (M⁺), 396, 352, 271, 242, 170, 142, 114, 70, 57 |
| 8g | 84 | 0.49 | −54.0° | 452 (M⁺), 396, 350, 327, 271, 242, 170, 142, 114, 70, 57 |
| 8h | 84 | 0.46 | −53.5° | 496 (M⁺), 440, 396, 271, 242, 182, 142, 114, 70, 57 |
| 8i | 93 | 0.36 | −56.0° | 463 (M⁺), 445, 352, 345, 271, 242, 170, 142, 114, 70, 57 |
| 8j | 97 | 0.51 | −72.0° | 478 (M⁺), 422, 377, 264, 208, 164, 152, 114, 70, 57 |
| 8k | 88 | 0.27 | −63.0° | 419 (M⁺), 346, 318, 277, 242, 204, 191, 149, 121, 114, 105, 93, 70, 57 |
| 8l | 90 | 0.49 | −52.0° | 432 (M⁺), 376, 332, 290, 219, 204, 142, 114, 91, 70, 57 |
| 8m | 100 | 0.49 | −118.5° | 476 (M⁺), 420, 375, 317, 242, 170, 162, 142, 114, 91, 70, 57 |
| 8n | 88 | 0.48 | −92.0° | 460 (M⁺), 386, 359, 330, 300, 286, 162, 142, 116, 114, 70, 57 |
| 8o | 58 | 0.43 | −132.5° | 426 (M⁺), 360, 325, 284, 242, 213, 198, 170, 142, 128, 114, 70, 57 |
| 8p | 66 | 0.41 | −122.0° | 397 (M⁺), 296, 271, 215, 184, 160, 142, 127, 114, 100, 70, 57 |
| 8q | 81 | 0.51 | −96.0° | 447 (M⁺), 346, 271, 235, 215, 177, 150, 142, 115, 114, 70, 57 |
| 8r | 92 | 0.40 | −73.0° | 441 (M⁺), 340, 271, 228, 213, 171, 144, 142, 114, 70, 57 |

[a]Yields are for the pure isolated product after chromatography.
[b]2:1 hexane-acetone
[c]4:1 CH₂Cl₂—EtOAc
[d]c = 0.2, CH₃OH.

General Method for Deprotection of Boc-Depsipeptides 8a–r

To a cooled (0° C.) and stirred solution of the appropriate dipeptide derivative (8a–r, 1 mmol) in $CH_2Cl_2$ (5 mL) is added TFA (5 mL) under an inert atmosphere. The solution is then stirred at this temperature for 1 hour, and the solvent is removed under reduced pressure. Residual TFA is removed azeotropically with toluene (3×20 mL), and the resulting oily trifluoroacetate salts (9a–r) are dried in vacuo and used directly in the subsequent reaction.

Z- and Boc-valyl-N-methylvalyl-proline (10a,b). The scaleup preparation of Z-Val-N-Me-Val-Pro (10a) was based on one of an earlier procedure reported by Dr. Pettit (see: PETTIT, G. R., et al. 1991, Antineoplastic agents 220, Synthesis of natural (−)-dolastatin 15, *Journal of the American Chemical Society*, 113, 6692). The same method used to synthesize Boc-valyl-N-methylvalyl-proline (10b) is used here as is now described.

To a solution of t-Boc-valine (6.64 g, 30.5 mmol, 2 eq.) in dry $CH_2CL_2$ (100 mL) cooled to −23° C. under Ar is added NMM (6.70 mL, 61.1 mmol, 4 eq.) and pivaloyl chloride (3.76 mL, 30.5 mmol, 2 eq). After 3 hours at this temperature, a cooled (−23° C.) solution of N-methyl-L-valyl-O-methyl-L-proline (5.3 mmol; 3.7 g) in dry $CH_2Cl_2$ (15 mL) is slowly added. The reaction is allowed to proceed for 4 hours at this temperature and for 24 hours at room temperature. The reaction mixture is then washed with saturated citric solution (3×100 mL), water (100 mL), saturated $NaHCO_3$ solution (2×100 mL), and water (100 mL). The organic phase is dried and the solvent is evaporated to give a straw-colored oil. Flash chromatography (silica gel, 2.5″×18″ column, 15% acetone-hexane as eluent) led to 6.5 g (97%) of the pure dipeptide as a colorless oil: $[\alpha]_D^{25}$=−187° (c=0.2). A 4.5-g (10.5 mmol) aliquot of the pure product is dissolved in 100 mL of 1:1 EtOH-$H_2O$, and 1 N NaOH (17 mL) is added. The mixture is vigorously stirred until saponification is complete as judged by TLC (2 hours), and the clear solution is concentrated to one-half volume under reduced pressure. The solution is then acidified to pH 3 with 1 N HCl, and the product is extracted with EtOAc (3×60 mL). The combined solvent extract is dried ($Na_2SO_4$) and concentrated in vacuo to give the pure tripeptide acid as a colorless glass (4.26 g, 98%). $R_f$ 0.24 (hexane-EtOAc-AcOH, 8:2:1); $[\alpha]_D^{25}$=−188° (c=0.2); MS m/z 427 (1, M⁺), 312 (3), 285 (3), 257 (2), 229 (4), 199 (7), 185 (5), 170 (4), 144 (5), 116 (23), 86 (100), 84 (21), 72 (28), 70 (14), 57 (35); ¹H NMR (300 MHz, $CDCl_3$) δ 0.86 (d, J=6.6 Hz, 3H, Val $CH_3$), 0.91 (d, J=6.6 Hz, 6H, 2×Val $CH_3$), 0.97 (d, J=6.9 Hz, 3H, Val $CH_3$), 1.42 (s, 9H, t-butyl), 1.84–2.40 (m, 6H, 2×Val $CH_\beta$, 2×Pro $CH_2$), 3.15 (s, 3H, N—$CH_3$), 3.62–3.71 (m, 1H, ½ Pro $CH_2$), 3.87–3.97 (m, 1H, ½ Pro $CH_2$), 4.42 (dd, $J_1$=9.3 Hz, $J_2$=7.2 Hz, 1H, Val $CH_\alpha$), 4.49 (dd, $J_1$=7.5 Hz, $J_2$=6.3 Hz, 1H, Pro $CH_\alpha$), 5.00 (d, J=10.8 Hz, 1H, N-Me-Val $CH_\alpha$), 5.22 (bd, J=9.3 Hz, 1H, NH). Anal. Calcd. For $C_{22}H_{36}N_3O_6$: C, 59.84; H, 8.90; N, 9.52. Found: C,. 59.61; H, 9.04; N, 9.34.

General Procedure for Synthesis of Z- or Boc-depsipeptides 11a–r

N-[(2S)-O-[[N-(Bezyloxycarbonyl)-valyl]-(N-methyl-valyl)-prolyl-prolyl]-2-hydroxyisovaleryl]-2-phenethylamide (11c). Amide 8c (0.35 g, 0.84 mmol) was deprotected in 1:1 TFA-$CH_2Cl_2$ (10 mL) at 0° C. for 1 hour to yield trifluoroacetate salt 9c as an oil (after drying in vacuo 1 hour). To a cooled (ice-bath) mixture of amide 9c (0.27 g, 0.84 mmol) and Z-tripeptide 10a (0.37 g, 0.80 mmol) in dry $CH_2Cl_2$ (10 mL) is added $Et_3N$ (0.23 mL, 1.68 mmol) and DEPC (0.13 mL, 0.88 mmol). The clear solution is stirred for 2 hours at 0° C., 18 hours at room temperature, and then concentrated. The product is separated by silica gel chromatography (1″×16″ column) with 1:3 acetone-hexane as eluent. The appropriate fractions are combined and concentrated to give the tetrapeptide (11c) as a colorless glass (0.61 g, 100%). $R_f$ 0.43 (hexane-acetone, 1:1); $[\alpha]_D^{25}$−185° (c=0.1); MS m/z 761 (0.5, M⁺), 6.53 (5), 562 (3), 499 (2), 442 (4), 416 (12), 347 (38), 324 (12), 239 (100), 211 (42), 196 (9), 139 (4), 109 (47); ¹H NMR (300 MHz, $CDCl_3$) δ 0.80–0.95 (m, 15H, 5×Val $CH_3$), 1.02 (d, J=6.6 Hz, 3H, Val $CH_3$), 1.82–2.35 (m, 10H, 2×Val $CH_\beta$, 4×Pro $CH_2$), 2.43 (spd, $J_1$=6.9 Mz, $J_2$=3.3 Hz, 1H, Hiva $CH_\beta$), 2.83 (t, J=7.5 Hz, 2H, Ph-$CH_2$), 3.15 (s, 3H, N—$CH_3$), 3.35–3.52 (m, 2H, Pro $CH_2$), 3.55–3.70 (m, 2H, N—$CH_2$), 3.83–3.92 (m, 1H, ½ Pro $CH_2$), 3.96–4.06 (m, 1H, ½ Pro $CH_2$), 4.52 (dd, $J_1$=9.0 Hz, $J_2$=6.3 Hz, 1H, $CH_\alpha$), 4.58–4.66 (m, 2H, 2×$CH_\alpha$), 5.07 (d, J=12.0 Hz, 1H, N-Me-Val $CH_\alpha$), 5.08 (d, J=3.0 Hz, 1H, Hiva $CH_\alpha$), 5.10 (s, 2H, Ph-$CH_2$—O), 5.42 (bd, J=9.3 Hz, 1H, NH), 7.17–7.40 (m, 10H, ArH).

For the physical properties of compounds 11a–r, see Table III, below.

TABLE III

Physical constants for pentapeptide derivatives 11a–r.

| Compound | % yield[a] | $R_f$[b] | $[\alpha]_D^{25}$[d] | MS |
|---|---|---|---|---|
| 11a | 86 | 0.42 | −199° | 733 (M$^+$), 625, 583, 527, 471, 414, 291, 239, 211 |
| 11b | 64 | 0.52 | −175° | 747 (M$^+$), 639, 541, 485, 428, 402, 347, 305, 239, 211, 181, 139, 108 |
| 11c | 100 | 0.43 | −185° | 761 (M$^+$), 653, 562, 499, 442, 416, 347, 324, 239, 211, 196, 139, 109 |
| 11d | 92 | 0.46 | −195° | 745 (M$^+$), 645, 574, 517, 460, 434, 337, 313, 257, 239, 213, 181, 170, 142, 123, 115, 110 |
| 11e | 91 | 0.39 | −208° | 795 (M$^+$), 687, 589, 533, 476, 347, 324, 239, 211, 196, 181, 149 |
| 11f | 84 | 0.46 | −161° | 761 (M$^+$), 733, 690, 661, 590, 533, 477, 450, 407, 353, 313, 257, 239, 213, 198, 181, 170, 154 |
| 11g | 95 | 0.43 | −192° | 761 (M$^+$), 661, 636, 589, 533, 477, 450, 410, 353, 313, 257, 239, 213, 198, 181, 171, 154 |
| 11h | 88 | 0.47 | −180° | 806 (M$^+$), 707, 636, 579, 577, 522, 494, 397, 313, 257, 239, 213, 185, 181, 166, 154 |
| 11i | 86 | 0.43 | −138° | 772 (M$^+$), 636, 600, 584, 574, 410, 364, 313, 257, 239, 213, 198, 185, 181, 166, 154, 143, 117 |
| 11j | 67 | 0.39 | −216° | 821 (M$^+$), 713, 616, 615, 559, 502, 475, 379, 347, 239, 211, 164, 151, 108 |
| 11k | 83 | 0.34 | −158° | 762 (M$^+$), 654, 557, 500, 445, 417, 390, 374, 347, 277, 239, 211, 149, 121, 108 |
| 11l | 83 | 0.49 | −173°[e] | 775 (M$^+$), 667, 624, 569, 513, 456, 430, 347, 239, 211, 196, 181, 162 |
| 11m | 91 | 0.28[e] | −178° | 819 (M$^+$), 711, 613, 557, 500, 474, 377, 347, 239, 162 |
| 11n | 96 | 0.47 | −217° | 769 (M$^+$), 695, 669, 597, 541, 527, 485, 458, 410, 383, 361, 313, 257, 239, 213, 198, 181, 142, 116 |
| 11o | 78 | 0.33 | −289° | 769 (M$^+$), 563, 507, 424, 347, 327, 239, 211, 162, 129 |
| 11p | 98 | 0.52 | −193° | 706 (M$^+$), 633, 606, 591, 535, 508, 478, 422, 410, 395, 367, 325, 313, 257, 239, 213, 198, 181, 170, 142, 116 |
| 11q | 100 | 0.57 | −211° | 756 (M$^+$), 683, 585, 528, 513, 472, 445, 417, 375, 313, 257, 239, 213, 198, 177, 150, 116 |
| 11r | 99 | 0.23[e] | −189° | 784 (M$^+$), 676, 633, 579, 522, 466, 437, 396, 369, 347, 240, 227, 211, 213, 196, 171, 144, 125, 108 |

[a]Yields are for the pure isolated product after chromatography.
[b]1:1 hexane-acetone
[c]2:1 hexane-acetone
[d]c = 0.1, CH$_3$OH
[e]c = 0.2, CH$_3$OH.

General Procedure for Deprotection of Z- or Boc-Depsipeptides 11a–r

Method A (Z-Depsipeptides)

A solution of the appropriate Z-depsipeptide (0.1 mmol) in EtOAc (20 mL) is prepared, and 0.8 mmol of 10% Pd/C catalyst is added under a blanket of Ar. The solution is then vigorously stirred under hydrogen for 18 hours, and the catalyst is removed by filtration through CELITE. The resulting clear solution is concentrated in vacuo to give the corresponding free amine as a viscous oil, which is used directly in the subsequent coupling step.

Method B (Boc-Depsipeptides)

To a cooled (0° C.) and stirred solution of the Boc-tetrapeptide derivative (0.5 mmol) in CH$_2$Cl$_2$ (2.5 mL) is added TFA (2.5 mL) under Ar. The solution is stirred at this temperature for 1 hour. Removal of solvent under reduced pressure affords an oil. Residual TFA is removed azeotropically with toluene (3×20 mL) to give the trifluoroacetate salt as a glassy solid which is dried in vacuo and used directly in the subsequent reaction step.

Method C (Employing Z-Depsipeptide 11e)

A 0.48-g sample of compound 11e is suspended in 0.5 mL of glacial acetic acid, and 1.5 mL of 33% HBr/AcOH reagent is slowly added with stirring. After the evolution of CO$_2$ ceased (30 min), ethyl ether (15 mL) is added, and the solution is cooled. After several minutes, an oil, which is a mixture of deprotected peptide and unchanged starting material, separates from solution. The product is isolated and the ethereal solution is adjusted to pH ~8 with saturated NaHCO$_3$ solution, followed by extraction with EtOAc (3×50 mL). The organic phase is concentrated to give a yellow glassy solid that is dried in vacuo and used without further purification in the next reaction.

General Procedure for Coupling of Dolavaline 4 With the Deprotected Depsipeptides to Give New Dolastatin 15 Derivatives 12a–r N-[(2S)-O-[(N,N-Dimethyl-valyl)-valyl-(N-methyl-valyl)-prolyl-prolyl]-2-hydroxyisovalerlyl]-2-phenethylamide (12c). Depsipeptide 11c (0.37 g, 0.49 mmol) is deprotected by catalytic hydrogenolysis (Method A) to afford an oil, which is dissolved in CH$_2$Cl$_2$ (10 mL) and cooled to 0° C. under Ar. To the solution is added dolavaline (4, 71 mg, 0.58 mmol), Et$_3$N (0.081 mL, 0.58 mmol) and DEPC (0.088 mL, 0.58 mmol), dropwise. After 2 hours, the solvent is removed under reduced pressure to yield an oil. Purification by flash chromatography (silica gel, 1"×16" column, 3:2 hexane-acetone), is followed by rapid gel permeation chromatography on SEPHADEX LH-20 (CH$_3$OH elution) to provide a colorless foam (0.26 g, 71%). R$_f$ 0.21 (hexane-acetone, 2:1); $[\alpha]_D^{25}$ −206° (c=0.1); MS m/z 754 (1, M$^+$), 711 (2), 663 (0.5), 499 (0.5), 437 (3.5), 416 (5), 340 (32), 324 (5), 239 (4), 227 (7), 211 (5), 196 (9), 196 (10), 154 (5), 109 (9), 101 (59), 100 (100); IR (NaCl) $v_{max}$ 3312, 2963, 2934, 2874, 1744, 1638, 1535, 1497, 1443, 1279, 1204, 1186, 1096, 1038, 1003 cm$^{-1}$; $^1$H NMR (300 MHz, CDCl$_3$) δ 0.78 (d, J=6.6 Hz, 3H, Val CH$_3$), 0.83 (d, J=6.6 Hz, 3H, Val CH$_3$), 0.89–0.98 (m, 12H, 5×Val CH$_3$), 1.00 (d, J=6.6 Hz, 6H, 2×Val CH$_3$), 1.74–2.43 (m, 12H, Hiva CH$_\beta$, 3×Val CH$_\beta$, 4×Pro CH$_2$), 2.24 (s, 6H, 2×Dov CH$_3$), 2.45 (d, J=6.0 Hz, 1H, Dov CH$_\alpha$), 2.82 (t, J=7.8 Hz, 2H, Ph-CH$_2$), 3.20 (s, 3H, N—CH$_3$), 3.38–3.51 (m, 2H, Pro CH$_2$), 3.56–3.71 (m, 2H, N—CH$_2$), 3.83–3.94 (m, 1H, ½ Pro CH$_2$), 3.96–4.06 (m, 1H, ½ Pro CH$_2$), 4.59–4.68 (m, 2H, 2×CH$_\alpha$), 4.79 (dd, J$_1$=9.0 Hz, J$_2$=6.9 Hz, 1H, CH$_\alpha$), 5.09 (d, J=3.0 Hz, 1H, Hiva CH$_\alpha$), 5.11 (d, J=12.0 Hz, 1H, N-Me-Val CH$_\alpha$), 6.89 (bd, J=9.3 Hz, 1H, NH), 7.17–7.31 (m, 5H, ArH), 7.39 (bs, 1H, NH); $^{13}$C NMR (500 MHz, CDCl$_3$) δ 16.5, 17.6, 18.2, 18.6, 18.9, 19.2, 19.5, 20.2, 25.1, 25.2, 27.4, 27.7, 28.4, 29.3, 29.8, 30.7, 31.1, 35.4, 40.8, 43.0, 47.1, 47.8, 53.7, 57.9, 59.1, 59.6, 76.5, 78.6, 126.3, 128.4 (2), 128.7 (2), 139.0, 169.1, 169.4, 170.7, 171.5, 171.8, 173.2. Anal. Calcd for C$_{40}$H$_{66}$N$_6$O$_7$.1/2H$_2$O: C, 64.46; H, 8.84; N, 11.00. Found: C, 64.69; H, 9.00; N, 10.77.

For the physical properties of compounds 12a–r, see Table IV.

TABLE IV

Physical constants for dolastatin 15 structural modifications 12a–r.

| Compound | % yield[a] | $R_f$[b] | $[\alpha]_D^{25}$[d] | MS |
|---|---|---|---|---|
| 12a | 87 | 0.32 | −234° | 726 (M+), 682, 526, 437, 415, 388, 340, 296, 255, 239, 227, 211, 197, 182, 170, 150 |
| 12b | 92 | 0.49 | −183° | 740 (M+), 697, 485, 437, 429, 402, 347, 340, 239, 211, 197, 182, 154, 141, 139, 120, 106, 101, 100 |
| 12c | 71 | 0.21[c] | −206° | 754 (M+), 711, 663, 499, 437, 416, 340, 324, 239, 227, 211, 196, 154, 109, 101, 100 |
| 12d | 79 | 0.27 | −215° | 772 (M+), 729, 663, 573, 437, 340, 324, 238, 227, 210, 196, 182 |
| 12e | n.d. | 0.33 | −185° | 788 (M+), 745, 663, 589, 563, 533, 477, 450, 436, 340, 324, 255, 239, 227, 211, 196, 182 |
| 12f | 83 | 0.27 | −179° | 788 (M+), 745, 663, 534, 475, 450, 437, 408, 340, 324, 296, 239, 227, 211, 206, 197, 182, 169, 154 |
| 12g | 82 | 0.31 | −167° | 788 (M+), 745, 663, 585, 533, 476, 450, 408, 340, 324, 296, 239, 227, 211, 206, 197, 182, 169, 154 |
| 12h | 84 | 0.29 | −177° | 834 (M+), 791, 663, 521, 494, 437, 340, 324, 312, 296, 239, 227, 211, 206, 197, 182, 169, 154 |
| 12i | 90 | 0.28 | −183° | 799 (M+), 780, 756, 663, 600, 544, 530, 487, 461, 437, 354, 340, 324, 296, 239, 227, 211, 197, 182, 169, 154 |
| 12j | 75 | 0.23 | −169° | 814 (M+), 771, 476, 437, 340, 239, 227, 211, 172, 164, 151, 101, 100 |
| 12k | 65 | 0.19 | −163° | 755 (M+), 712, 437, 417, 339, 296, 277, 239, 227, 211, 196, 182, 149, 121, 108, 101, 100 |
| 12l | 89 | 0.44 | [e]−164° | 768 (M+), 725, 569, 513, 433, 430, 340, 296, 262, 239, 226, 211, 196, 181, 155 |
| 12m | 40 | 0.34 | −211° | 812 (M+), 770, 613, 557, 500, 474, 437, 414, 382, 340, 296, 239, 227, 211, 197, 182, 154, 141, 120, 101, 100 |
| 12n | 82 | 0.35 | −132° | 796 (M+), 753, 722, 484, 458, 437, 340, 239, 227, 211, 198, 182, 154, 101, 100 |
| 12o | 78 | 0.21 | −292° | 762 (M+), 719, 507, 451, 436, 424, 364, 339, 296, 255, 241, 227, 211, 197, 182, 164, 154 |
| 12p | 72 | 0.34 | −174° | 733 (M+), 690, 437, 395, 340, 296, 239, 227, 211, 198, 182, 154, 127, 101, 100 |
| 12q | 80 | 0.35 | −181° | 783 (M+), 740, 548, 528, 514, 472, 457, 445, 437, 417, 375, 340, 239, 227, 211, 198, 182, 177, 150, 101, 100 |
| 12r | 91 | 0.29 | −192° | 777 (M+), 734, 466, 437, 369, 340, 296, 239, 227, 211, 197, 182, 171, 144, 128, 114, 101, 100 |

[a]Yields are for the pure isolated product after chromatography.
[b]1:1 hexane-acetone
[c]2:1 hexane-acetone
[d]c = 0.1, CH₃OH
[e]c = 0.2, CH₃OH.

Both dolastatin 10 (see: BAI, R., et al., 1990a, Dolastatin 10, a powerful cytostatic peptide derived from a marine animal: Inhibition of tubulin polymerization mediated through the vinca alkaloid binding domain, *Biochemical Pharmacology*, 39, 1941) and dolastatin 15 (see: BAI et al., 1992, Dolastatin 15, a potent antimitotic depsipeptide derived from *Dolabella auricularia*: Interaction with tubulin and effects on cellular microtubules, *Biochemical Pharmacology*, 43, 2637) interact with tubulin and cause arrest of cellular mitosis. Effects on tubulin in vitro with dolastatin 10 have been studied in detail (see: BAI et al., 1990b; Binding of dolastatin 10 to tubulin at a distinct site for peptide antimitotic agents near the exchangeable nucleotide and vinca alkaloid sites, *Journal of Biological Chemistry*, 265, 17141; and BAI et al., 1995, Interaction of dolastatin 10 with tubulin: Induction of aggregation and binding and dissociation reactions, *Molecular Pharmacology*, 47, 965). Since the interaction of dolastatin 15 with tubulin appears considerably weaker, less attention has been given to the biochemical properties of this depsipeptide. Nevertheless, a number of studies have described the antiproliferative effects of dolastatin 15 against human lymphoma cells (see: BECKWITH et al., 1993, Growth inhibition of human lymphoma cell lines by the marine natural products dolastatins 10 and 15, *Journal of the National Cancer Institute*, 85, 483) on murine bone marrow progenitor cells (see: JACOBSEN et al., 1991, Antineoplastic dolastatins: Potent inhibitors of hematopoietic progenitor cells, *Journal of the National Cancer Institute*, 83, 1672), and on malignant peripheral blood cells from patients with acute myeloid leukemia (see: STEUBE et al., 1992, Dolastatin 10 and dolastatin 15: Effects of two natural peptides on growth and differentiation of leukemia cells, *Leukemia*, 6, 1048).

All of these investigations were made possible by the synthesis (see: PETTIT et al., 1991, Antineoplastic agents 220, Synthesis of natural (−)-dolastatin 15, *Journal of the American Chemical Society*, 113, 6692) of dolastatin 15 at the Cancer Research Institute in Tempe, Ariz. which provided the first synthetic specimens of the peptide available anywhere. A subsequent, modified synthetic procedure (see: PETTIT et al., 1994, The dolastatins, 20, A convenient synthetic route to dolastatin 15, *Tetrahedron*, 50, 12097) proved very practical for large-scale preparation of this promising anticancer drug. Still another synthesis of dolastatin 15 derived subsequent to Pettit's original synthesis, is described by Patino et al. (see: PATINO et al., 1992, Total synthesis of the proposed structure of dolastatin 15, *Tetrahedron*, 48, 4115–4122). The potential advantage of identifying suitable substitutions for the Dpy unit of dolastatin 15 became apparent at the start of the efforts to synthesize a commercially viable alternative. Most significant was the potential exclusion of six synthetic steps, and the elimination of the unpredictable dolapyrrolidinone cyclization sequence. Thus it was determined to replace the modified amino acid unit with readily available arylalkylamines based on β-phenethylamine, and with various other groups.

For the preparation of α-hydroxy amides 7a–r, it was determined most efficient to obtain these substances without protection of the hydroxyl group. For the aliphatic amines 6b–o, this objective was readily met by using Pettit's original synthetic approach (op. cit.). Thus 2-(S)-hydroxyisovaleric acid (Hiva, 3) and the appropriate amine were condensed by use of DEPC with NMM as base to give compounds 7b–o in good yield as shown in Scheme 1. Owing to the reduced nucleophilicity of the amino component, acylation of the aromatic amines (6a, 6p–r) with activated Hiva was more challenging. Mild coupling reagents such as DEPC (see: YAMADA et al., 1975, Diphenyl phosphorazidate (DPPA) and diethyl phosphorocyanidate (DEPC), Two new reagents for solid-phase peptide synthesis and their application to the synthesis of porcine motilin, *Journal of the Amerian Chemical Society*, 97, 7174); WRK (see: PETTIT et al., 1966, Structural biochemistry II, Synthesis of 3β-Hydroxy-17β-(L-prolyl-L-prolyl) amino-5α-androstane, *Canadian Journal of Chemistry*, 44, 2023; and PETTIT et al., 1967, Synthesis of 3β-Acetoxy-17β-(L-arginyl-L-arginyl-L-prolyl)amino-5α-androstane, *J. Med. Chem.*, 10, 145) produced no reaction, whereas strong activation with DCC, BrOP (see: COSTE et al., 1990, A new reagent for coupling N-methylated amino acids, *Tetrahedron Letters*, 31, 669) or with various chloroformates (see: VAN BOGART et al., 1993, Synthesis and antitrypanosomal evaluation of some thiazole-containing amino acids and peptides, *European Journal of Medicinal Chemistry*, 28, 387; and NEDEV et al., 1993, A convenient method for synthesis of Fmoc-amino acid p-nitroanilides based on isobutyl chloroformate as condensation agent, *Tetrahedron Letters*, 34, 4201) allowed competitive esterification of the unprotected α-hydroxyl group, giving rise to complex mixtures. However, the HOBt ester of Hiva, prepared in situ with DCC at 0° C. in anhydrous THF, was found to be very suitable for selective acylation of such aromatic amines. Indeed, the result was moderate to good yields of the desired amide with no trace of esterification side-products. In the subsequent step, Boc-proline was esterified with alcohols 7a–r by use of DCC in $CH_2Cl_2$ with 4-pyrrolidinopyridine as catalyst (room temperature, 18 hours) to afford excellent yields of esters 8a–r as viscous oils. It was then discovered that the water-soluble carbodilmide EDC-HCl wvorked equally well and gave fewer purification problems than DCC. The Boc protecting group was removed with TFA to yield the corresponding trifluoroacetates 9a–r.

For the synthesis and subsequent deblocking of depsipeptides 11a–r, it was first thought to use the Z- protection scheme which was first described in the original synthesis of dolastatin 15 (see U.S. Pat. No. 4,879,278). However, the conditions of catalytic hydrogenolysis used to remove this group proved unsuitable for several of the peptide intermediates as reported below. Consequently, Boc-valyl-N-methylvalylproline (10b) was synthesized in addition to the usual Z-tripeptide intermediate (10a), in order to circumvent catalytic hydrogenolysis. The DEPC-mediated segment condensation of the appropriate tripeptide (10a or 10b) with trifluoroacetates 9a–r gave consistently high yields of the corresponding depsipeptide derivative (11a–r) as shown in Scheme 2.

The mild catalytic hydrogenolysis conditions previously used to remove the Z-protecting group were found to cause quantitative dechlorination of compound 11e and therefore forced the development of an alternative route for the halogenated aromatic amides 9d–h. Although attempted deprotection of peptide 11e with 33% hydrogen bromide in glacial acetic acid under the usual conditions caused no loss of halogen, extensive racemization of at least one of the amino acid units was observed, which quite likely is the strong-acid sensitive N-Me-Val unit, as reported by Benoiton et al. (see: BENOITON et al., 1973, N-methylamino acids in peptide synthesis, III, Racemization during deprotection by saponification and acidolysis, *Canadian Journal of Chemistry*, 51, 2555). Thus, all remaining peptides that contained halogenated aromatic rings were prepared as Boc-protected depsipeptides (11d, 11f–h). Deprotection of these peptides in $TFA-CH_2Cl_2$ (1:1) at 0° C. for 1 hour proceeded smoothly and gave quantitative yields of the corresponding trifluoroacetate salts (used directly in the subsequent coupling reactions). The Boc-strategy was also utilized for the p-nitro-phenethylamine (11i), Met-OMe (11n), thiazole (11p), and benzothiazole (11q) amides in order to avoid unwanted nitro group reduction or catalyst poisoning by the sulfur-containing peptides. Deprotection of all other peptide intermediates by catalytic hydrogenolysis (10% Pd/C, EtOAc, 18 hours) gave the corresponding amines in excellent yields.

Final coupling of each peptide to the N-terminal dolavaline residue was accomplished in good yield with DEPC/$Et_3N$ in $CH_2Cl_2$ as shown in Scheme 3. In some cases, owing to the basic nature of the final peptides 12a–r, further purification is necessary following silica gel chromatography. In such cases, rapid gel permeation chromatography (SEPHADEX LH-20 methanol elution) gave very satisfactory results, affording the final peptides as colorless foams or amorphous powders.

Results of in vtro testing of the synthetic derivatives (12a–r) against the murine leukemia cell lines P388 and L1210 and the human Burkitt lymphoma CA46 line, along with the corresponding tubulin anti-polymerization results, are reported in Table V, below.

TABLE V

Inhibitory activities of dolastatin 15 (1) and synthetic modifications (12a–r) on murine P388 lymphocytic leukemia [$ED_{50}$ (ng/mL)][a], murine L1210 leukemia [$IC_{50}$ (nM)][b], human CA46 Burkitt lymphoma [$IC_{50}$ (nM)][b,c], and tubulin polymerization ($IC_{50}$ (:M) ± [SD]).

| Compound | Mouse Leukemia P388 | Mouse Leukemia L1210 | Human CA46 Burkitt Lymphoma | % Mitotic Cells | Tubulin Polymerization |
|---|---|---|---|---|---|
| 1 | 2.4 | 4 | 2 | 31 | 5.2 [0.6] |
| 12a | 0.52 | 3 | 2 | 26 | 26 [6] |
| 12b | 0.42 | 1 | 0.3 | 46 | 20 [3] |
| 12c | 0.26 | 2 | 0.3 | 45 | 15 [1] |
| 12d | 0.55 | 4 | 0.8 | 46 | 12 [2] |
| 12e | 0.49 | d | d | d | d |
| 12f | 0.37 | 4 | 2 | 38 | 14 [2] |
| 12g | 0.33 | 4 | 2 | 26 | 10 [2] |
| 12h | 0.36 | 2 | 2 | 48 | 11 [2] |
| 12i | 0.60 | 4 | 3 | 36 | 11 [2] |
| 12j | 0.40 | 2 | 0.8 | 31 | 21 [2] |
| 12k | 0.40 | 4 | 2 | 30 | 20 [3] |
| 12l | 0.38 | d | d | d | d |
| 12m | 0.54 | 3 | 1 | 40 | 13 [3] |
| 12n | 0.55 | 3 | 3 | 44 | 18 [4] |
| 12o | 3.1 | 4 | 2 | 42 | 24 [2] |
| 12p | 0.26 | 2 | 4 | 40 | 8.4 [1] |
| 12q | 0.45 | 3 | 2 | 36 | 9.3 [2] |
| 12r | 0.29 | 2 | 2 | 42 | 16 [2] |

[a]$ED_{50}$ (P388) and $IC_{50}$ (L1210) refer to the drug dosages required to inhibit tumor cell growth by 50%. There is no mathematical difference between the two values which were both calculated identically in the present study.
[b]L1210 cells were counted after 24 hours of growth, CA46 cells after 20 hours.
[c]CA46 cells were treated with 80 nM drug for 20 hours; cells were harvested by centrifugation, fixed, and stained with Giemsa; control cells: 3% mitotic cells.
[d]Compounds 12e and 12l were not evaluated in this assay.

All of the derivatives showed antiproliferative activities quite comparable to the performance of the parent dolastatin 15 (1) and, in the Burkitt cells, all analogues caused a marked rise in the mitotic index. None, however, was as potent an inhibitor of tubulin polymerization as dolastatin 15 (1). Likewise, repetitive testing of 12a–r in the NCI's 60-cell-line human tumor primary screen consistently yielded mean panel $GI_{50}$ values of similar potency to that of the dolastatin 15 standard as shown in Table VI, below.

TABLE VI

Mean panel GI$_{50}$ values (nM) ± S.D.[a] and GI$_{50}$-Compare correlations[b] with dolastatin 15 for synthetic modifications (12a–r) tested[c] in the NCI 60-cell-line in vitro human tumor panel[d].

| Compound[e] | Mean Panel GI$_{50}$[a] | Dolastatin 15 Compare Coefficient[b] |
|---|---|---|
| 1   | 1.12 ± 0.50 | 1.00 |
| 12a | 1.25 ± 0.48 | 0.81 |
| 12b | 0.79 ± 0.10 | 0.74 |
| 12c | 1.06 ± 0.48 | 0.77 |
| 12d | 0.89 ± 0.29 | 0.77 |
| 12f | 0.83 ± 0.41 | 0.78 |
| 12g | 0.81 ± 0.31 | 0.78 |
| 12h | 0.81 ± 0.15 | 0.78 |
| 12i | 0.94 ± 0.41 | 0.79 |
| 12j | 1.50 ± 0.58 | 0.78 |
| 12k | 3.00 ± 1.04 | 0.81 |
| 12m | 3.76 ± 1.05 | 0.74 |
| 12n | 2.93 ± 0.93 | 0.80 |
| 12o | 4.48 ± 0.44 | 0.71 |
| 12p | 1.20 * | 0.79 |
| 12q | 2.54 * | 0.77 |
| 12r | 2.31 * | 0.78 |

[a]Results represent the averages ± S.D. of triplicate tests, except where indicated by an asterisk (*) which are duplicate tests only.
[b]Definitions and methods of Compare calculations are detailed in Boyd and Paull (1995).
[c]The screening assay procedures are detailed in Monks, et al. (1991); other details of the current screening assay model may be found in Boyd and Paull (1995).
[d]Further details of the rationale and background of the screen may be found in Boyd (1993).
[e]Compounds 12e and 12l were not tested.

Moreover, using the COMPARE analyses described by Boyd and Paull (see: BOYD, et al., 1995, Some practical considerations and applications of the National Cancer Institute in vitro anticancer drug discovery screen, *Drug Development Research*, 34, 91), the mean graph fingerprints of 12a–r in the NCI screen were all highly correlated (e.g., ≧0.7) with that of dolastatin 15. Thus, it was determined that the antiproliferative and antimitotic activities of dolastatin 15 are remarkably tolerant of changes in the C-terminal residue, whereas their antitubulin properties are more sensitive to such changes. These results are in contrast to analogous studies reported by Pettit et al.(see: PETTIT et al., 1995, Antineoplastic Agents 337, Synthesis of Dolastatin 10 Structural Modifications, *Anticancer Drug Design*, 10, 529) in which those derivatives of dolastatin 10 which had the C-terminal dolaphenine unit replaced with groups not containing a β-phenethylamine carbon skeleton displayed small differences in antitubulin potencies but encountered up to 100-fold decreases in cytoroxicity.

The interaction of dolastatin 15 with purified tubulin is considerably weaker than that of dolastatin 10 (about 20-fold) despite its potent antiproliferative effect on cellular microtubules (one-fourth as active as dolastatin 10, but ten times more active than the antitumor drug vinblastine) (see: BAI et al., 1992, Dolastatin 15, a potent antimitotic depsipeptide derived from *Dolabella auricularia*: Interaction with tubulin and effects on cellular microtubules, *Biochemical Pharmacology*, 43, 2637). In previous original studies on the antitubulin properties of dolastatin 15 reported by Bai et al. (see: Id.), the effects of this depsipeptide on the polymerization of 10 μM tubulin in 1 M monosodium glutamate-1 mM MgCl$_2$ were examined and provided an IC$_{50}$ value of 23 μM (50% inhibition of extent of polymerization after 20 min at 37° C.). This result was confirmed in new experiments, where a value of 19±0.3 (S.D.) μM was obtained. However, no IC$_{50}$ value was obtained for any of the dolastatin 15 derivatives presented herein under the reaction condition described, although clear inhibition of assembly rates did occur with these compounds (maximum concentration used, 40 μM).

With an increasing number of antimitotic drugs, particularly those that bind at the colchicine site, the tubulin polymers formed had a highly aberrant morphology in 1 M glutamate-1 mM MgCl$_2$ (see, for example, HAMEL et al., 1995, Limitations in the use of tubulin polymerization assays as a screen for the identification of new antimitotic agents: The potent marine natural product curacin A as an example, *Drug Development Research*, 3). Since these high molecular weight polymers, like microtubules, scatter light, they make it impossible to quantify drug effects by turbidimetry or centrifugation. In exploring alternate assay conditions for such compounds, it was discovered that the aberrant polymers were generally not formed in 0.8 M glutamate at 30° C. (no MgCl$_2$ added to reactions). Under this reaction condition the normal assembly reaction still occurred at a reduced reaction rate, and there was a substantial reduction in the IC$_{50}$ value obtained with agents that could be examined under both reaction conditions.

An aberrant polymer formation was not observed with dolastatin 15, even though such a reaction does occur with dolastatin 10 (see: BAI et al., 1995, Interaction of dolastatin 10 with tubulin: Induction of aggregation and binding and dissociation reactions, *Molecular Pharmacology*, 47, 965). Nevertheless, when dolastatin 15 was evaluated for inhibition of assembly in 0.8 M glutamate at 30° C., the reduced IC$_{50}$ value effect was again observed. A value of 5.2±0.6 μM was obtained. More importantly, with this reaction condition it was possible to perform a quantitative comparison of the dolastatin 15 analogue series described here (see Table V). Although none of the 16 compounds evaluated had an IC$_{50}$ value as low as that of dolastatin 15, unambiguous inhibitory effects were observed with all agents examined. The IC$_{50}$ values obtained ranged from 8.4 μM for compound 12p to 26 μM for 12a. Including dolastatin 15, there was a five-fold range in the IC$_{50}$ values obtained in this sequence of experiments.

The study of the interaction of dolastatin 15 with tubulin was performed in conjunction with an evaluation of the effects of the agent on the growth of murine L1210 leukemia cells and human CA46 Burkitt lymphoma cells (see: BAI et al., 1992, Dolastatin 15, a potent antimitotic depsipeptide derived from *Dolabella auricularia*: Interaction with tubulin and effects on cellular microtubules, *Biochemical Pharmacology*, 43, 2637). The effects of most of these new dolastatin 15 dervatives were examined on these same cell lines, and little difference was found between the compounds as reported in Table V.

With the L1210 cells, IC$_{50}$ values for cell growth were in the 1–4 nM range, and with the Burkitt cells the range of IC$_{50}$ values was 0.3–4 nM. Although the range of values observed was similar to the five-fold variation in lC$_{50}$ values for tubulin polymerization, there was little correlation between the values obtained for specific compounds. Thus, for example, dolastatin 15 was the most potent inhibitor of tubulin assembly, but it was among the least active compounds with the L1210 and Burkitt cells.

To further verify the assumption that this entire series of compounds is acting intracellularly by interfering with tubulin function, the drug-treated Burkitt cells for mitotic arrest were analyzed. As was observed previously for dolastatin 15 (see: BAI et al., 1992, Dolastatin 15, a potent antimitotic depsipeptide derived from *Dolabella auricularia*: Interaction with tubulin and effects on cellular microtubules, *Biochemical Pharmacology*, 43, 2637), cells treated with all compounds at 80 nM caused the accumulation of high numbers of Burkirt cells in apparent metaphase arrest (Table V).

It has been suggested that the potent cytotoxicity and tubulin inhibitory effects of dolastatin 15 are not due to the parent molecule, but to more active metabolite derived therefrom. For instance, intracellular hydrolysis of the ester bond of the depsipeptide might produce a more potent peptide fragment or a fragment that is further metabolized to a more active species. This possibility seems consistent with the apparent insensitivity of dolastatin 15 activity to structural modification of the C-terminus and the recent observation by Roux, et al. (see: ROUX et al. 1994, Synthesis and in vitro cytotoxicity of diastereomerically modified dolastatin 15 analogues, Bioorganic and Medicinal Chemistry Letters, 4, 1947) that changes in the stereochemistry of the Hiva-Dpy unit are attended by minimal loss of cytotoxicity. Especially interesting here is the observation that the peptide segment N-dimethyl-L-valyl-L-valyl-N-methyl-L-valyl-L-prolyl-L-proline is apparently inactive while the synthetic dolastatin 15 derivative LU103793 reported by Dearruda et al. (see: DEARRRUDA et al. 1995, LU103793 (NSC D-669356): A synthetic peptide that interacts with microtubulcs, Cancer Research, 55, 3085), N-dimethyl-L-valyl-L-valyl-N-methyl-L-valyl-L-prolyl-L-prolyl-benzamide (NSC 669356), is both highly cytotoxic ($IC_{50}$, 3 nM against L1210 leukemia cells) and a potent inhibitor of tubulin polymerization ($IC_{50}$, 4.0±0.6 $\mu$M) under the same reaction conditions in which dolastatin 15 was 50% inhibitory at 5.2 $\mu$M. Alternatively, the benzamide derivative LU103793 may be necessary for proper transport of the peptide to the site(s) of activity.

It is now clear that the structurally unique Dpy unit of dolastatin 15 plays a very limited role in the cell growth inhibitory effects observed for dolastatin 15 and is probably not a critical component of the active site(s) of dolastatin 15. This fact presents an unusual opportunity to further enhance the ability to achieve the benefits of dolastatin 15 with a much simpler and cost effective manner and to optimize or otherwise exploit the in vivo antitumor effect of these unique compounds. It is thus apparent that the complex Dpy unit of dolastatin 15 can be readily replaced by amides derived from the more readily available phenethylamine, 2-aminothiazole, and 2-aminobenzothiazole, or by other relatively available and innocuous substituents without any significant diminution of cancer cell growth inhibitory activity of the resultant derivative.

Of nine bacteria and two fungi screened, dolastatin 15 and the eight derivatives described herein specifically inhibited growth of the enteric bacterium Erwinia carotovora (Table VII). The parent compound was the most active against E. carotovora.

TABLE VII

Minimum inhibitory concentrations ($\mu$g/disk) of dolastatin 15 and structural modifications for the bacterium Erwinia carotovora

| Peptide | Erwinia carotovora |
| --- | --- |
| Dolastatin 15 | 3.12–6.25 |
| 12b | 50–100 |
| 12c | 50–100 |
| 12j | 50–100 |
| 12k | 50–100 |
| 12m | 50–100 |
| 12p | 50–100 |
| 12q | 50–100 |
| 12r | 50–100 |

As used here, the bold numerals 1, 2 etc. refer to those compounds whose structures are shown below.

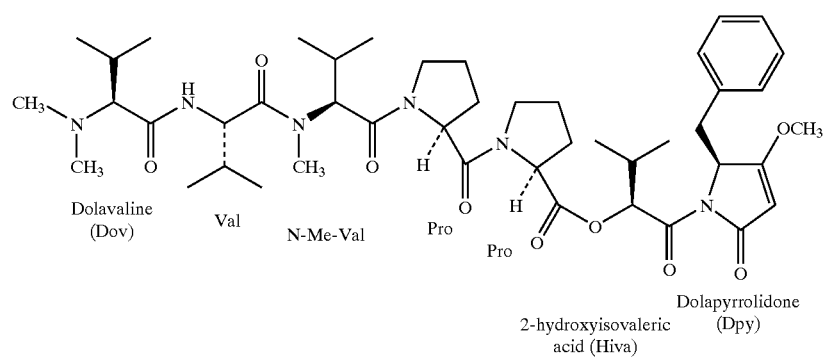

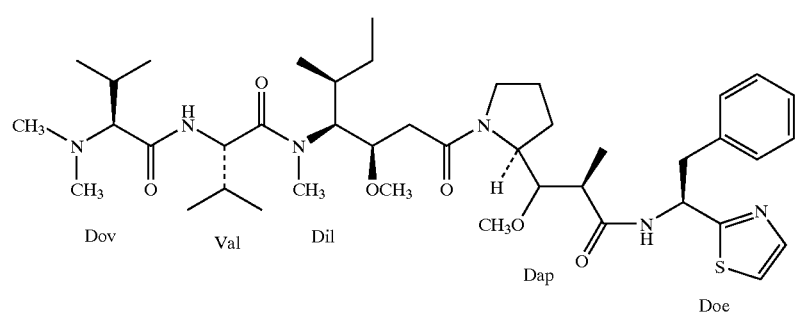

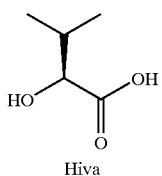
Hiva

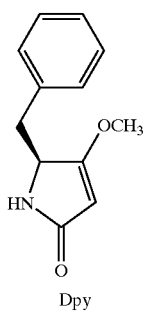
Dpy

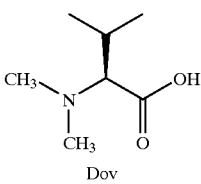
Dov

The synthesis of the depsidipeptide derivatives 9a–r is shown in Scheme 1 below.

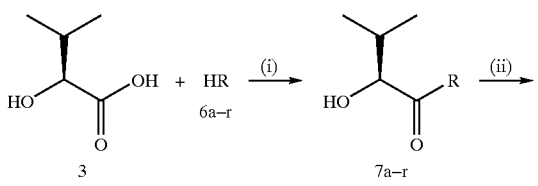

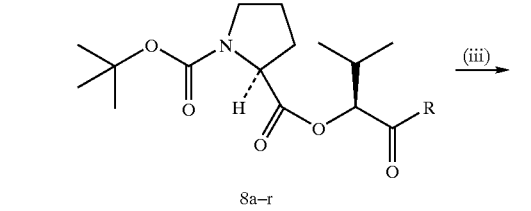

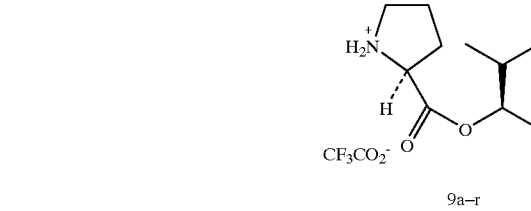

a) R=NHPh; Method A
b) R=NHCH$_2$Ph; Method A
c) R=NH(CH$_2$)$_2$Ph; Method A
d) R=NH(CH$_2$)$_2$-4-F-Ph; Method A
e) R=NH(CH$_2$)$_2$-4-Cl-Ph; Method A
f) R=NH(CH$_2$)$_2$-3-Cl-Ph; Method A
g) R=NH(CH$_2$)$_2$-2-Cl-Ph; Method A
h) R=NH(CH$_2$)$_2$-4-Br-Ph; Method A
i) R=NH(CH$_2$)$_2$-4-NO$_2$-Ph; Method A
j) R=NH(CH$_2$)$_2$-3,4-(CH$_3$O)$_2$Ph; Method A
k) R=NH(CH$_2$)$_2$-2-pyridine; Method A
l) R=NH(CH$_2$)$_3$Ph; Method A
m) R=L-Phe-OCH$_3$; Method A
n) R=L-Met-OCH$_3$; Method A
o) R=L-Pro-OCH$_3$; Method A
p) R=NH-2-thiazolyl; Method B
q) R=NH-2-benzothiazolyl; Method B
r) R=NH-3-quinolyl; Method B (i) Method A: DEPC, NMM, CH$_2$Cl$_2$, 0° C., 2 hours.
Method B: DCC, NOBt, (2 eq.), NMM, THF, 0 ° C., 2 hours.
(ii) Boc-L-Pro (1.2 eq.), DCC (1.2 eq.), 4-pyrrolidinopyridine (1.2 eq.), CH$_2$Cl$_2$ 23° C., 18 hours.

or

Boc-L-Pro (1.2 eq.), EDC-HCl (1.2 eq.), 4-pyrrolidinopyridine (2.4 eq.), CH$_2$Cl$_2$, 23° C., 18 hours.
(iii) TFA, CH$_2$Cl$_2$, 0° C., 1 hour.

The synthesis of Z- or Boc-pentapeptide derivatives 11a–r is shown in Scheme 2, below.

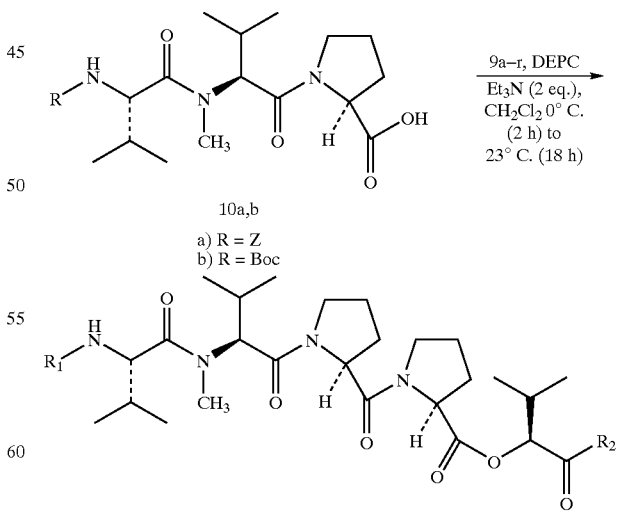

a) R = Z
b) R = Boc a) R$_1$=Z, R$_2$=NHPh
b) R$_1$=Z, R$_2$=NHCH$_2$Ph c) $R_1$=Z, $R_2$=NH(CH$_2$)$_2$Ph
d) $R_1$=Boc, $R_2$=NH(CH$_2$)$_2$-4-F-Ph
e) $R_1$=Z, $R_2$=NH(CH$_2$)$_2$-4-Cl-Ph
f) $R_1$=Boc, $R_2$=NH(CH$_2$)$_2$-3-Cl-Ph
g) $R_1$=Boc, $R_2$=NH(CH$_2$)$_2$-2-Cl-Ph
h) $R_1$=Boc, $R_2$=NH(CH$_2$)$_2$-4-Br-Ph Benzothiazolyl
i) $R_1$=Boc, $R_2$=NH(CH$_2$)$_2$-4-NO$_2$-Ph
j) $R_1$=Z, $R_2$=NH(CH$_2$)$_2$-3,4-(CH$_3$O)$_2$Ph
k) $R_1$=Z, $R_2$=NH(CH$_2$)$_2$-2-pyridine
l) $R_1$=Z, $R_2$=NH(CH$_2$)$_3$Ph
m) $R_1$=Z, $R_2$=L-Phe-OCH$_3$
n) $R_1$=Boc, $R_2$=L-Met-OCH$_3$
o) $R_1$=Z, $R_2$=L-Pro-OCH$_3$
p) $R_1$=Boc, $R_2$=NH-2-thiazolyl
q) $R_1$=Boc, $R_2$=NH-2-
r) $R_1$=Z, $R_2$=NH-3-quinolyl The synthesis of dolastatin 15 derivatives 12a–r is shown in Scheme 3, below.

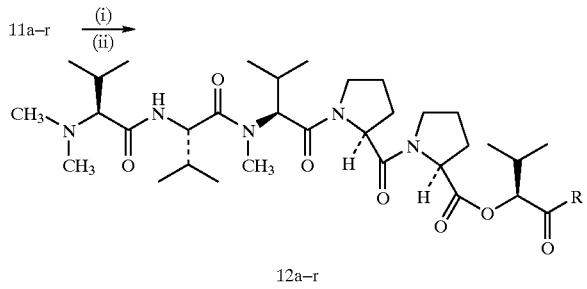

12a–r a) R=NHPh; Method A
b) R=NHCH$_2$Ph; Method A
c) R=NH(CH$_2$)$_2$Ph; Method A
d) R=NH(CH$_2$)$_2$-4-F-Ph; Method B
e) R=NH(CH$_2$)$_2$-4-Cl-Ph; Method C
f) R=NH(CH$_2$)$_2$-3-Cl-Ph; Method B
g) R=NH(CH$_2$)$_2$-2-Cl-Ph; Method B
h) R=NH(CH$_2$)$_2$-4-Br-Ph; Method B
i) R=NH(CH$_2$)$_2$-4-NO$_2$-Ph; Method B
j) R=NH(CH$_2$)$_2$-3,4-(CH$_3$O)$_2$Ph; Method A
k) R=NH(CH$_2$)$_2$-2-pyridine; Method A
l) R=NH(CH$_2$)$_3$Ph; Method A
m) R=L-Phe-OCH$_3$; Method A
n) R=L-Met-OCH$_3$; Method B
o) R=L-Pro-OCH$_3$; Method A
p) R=NH-2-thiazolyl; Method B
q) R=NH-2-benzothiazolyl; Method B
r) R=NH-3-quinolyl; Method A
(i) Methods A, B, or C.
Method A: H$_2$ 10% Pd/C, EtOAc, 18 hours.
Method B: TFA, CH$_2$Cl$_2$, 0° C., 1 hour.
Method C: 33% HBr/AcOH, 23° C., 30 minutes.
(ii) dolavaline (4, 1.2 eq.), DEPC (1.2 eq.), ET$_3$N (1.2 eq. with Method A; 2.4 eq. with Methods B or C), DEPC (1.2 eq.), CH$_2$Cl$_2$, 0° C., 2 hours.

What is claimed is:
1. A dolastatin 15 derivative of formula 13

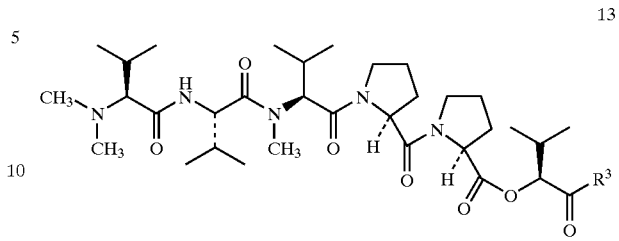

wherein $R^3$ is selected from the group consisting of:

NHPh, NHCH$_2$Ph, NH(CH$_2$)$_2$Ph, NH(CH$_2$)$_2$-4-F-Ph, NH(CH$_2$)$_2$-4-Cl-Ph, NH(CH$_2$)$_2$-3-Cl-Ph, NH(CH$_2$)$_2$-2-Cl-Ph, NH(CH$_2$)$_2$-4-Br-Ph, NH(CH$_2$)$_2$-4-NO$_2$-Ph, NH(CH$_2$)$_2$-3,4-(CH$_3$O)$_2$Ph, NH(CH$_2$)$_2$-2-pyridine, NH(CH$_2$)$_3$-Ph, L-Phe-OCH$_3$, L-Met-OCH$_3$, L-Pro-OCH$_3$, HN-2-thiazoly, NH-2-benzothiazolyl, and NH-3-quinolyl.

2. The dolastatin 15 derivative of claim 1, wherein $R^3$=NH(CH$_2$)$_2$Ph.

3. A method of synthesizing a dolastatin 15 derivative of formula 13

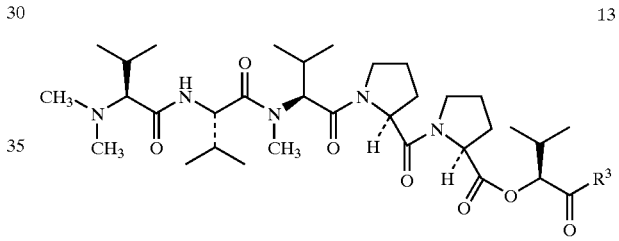

wherein $R^3$ is selected from the group consisting of:

NHPh, NHCH$_2$Ph, NH(CH$_2$)$_2$Ph, NH(CH$_2$)$_2$-4-F-Ph, NH(CH$_2$)$_2$-4-Cl-Ph, NH(CH$_2$)$_2$-3-Cl-Ph, NH(CH$_2$)$_2$-2-Cl-Ph, NH(CH$_2$)$_2$-4-Br-Ph, NH(CH$_2$)$_2$-4-NO$_2$-Ph, NH(CH$_2$)$_2$-3,4-(CH$_3$O)$_2$Ph, NH(CH$_2$)$_2$-2-pyridine, NH(CH$_2$)$_3$-Ph, L-Phe-OCH$_3$, L-Met-OCH$_3$, L-Pro-OCH$_3$, NH-2-thiazolyl, NH-2-benzothiazolyl, and NH-3-quinolyl;

said method comprising:
(a) reacting 2-hydroxyisovaleric acid with an amine of formula $R^3$-H for a time and under conditions effective to form an amide of formula 14

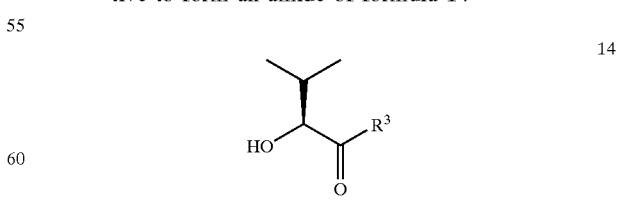

wherein $R^3$ is as defined above;
(b) reacting the amide of formula 14 with tBoc-L-proline for a time and under conditions effective to form an ester of formula 15

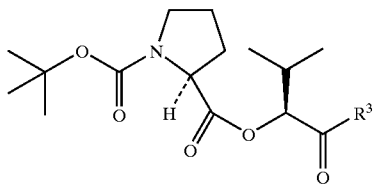

15

(c) treating the ester of formula 15 with trifluoroacetic acid for a time and under conditions effective to remove the tBoc group from the ester of formula 15, thereby generating a trifluoroacetic acid salt of formula 16

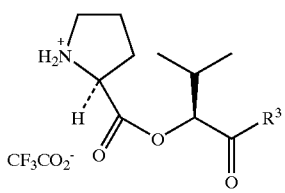

16

(d) reacting the trifluoroacetic acid salt of formula 16 with the tripeptide of formula 17 for a time and under conditions effective to generate the tetrapeptide of formula 18

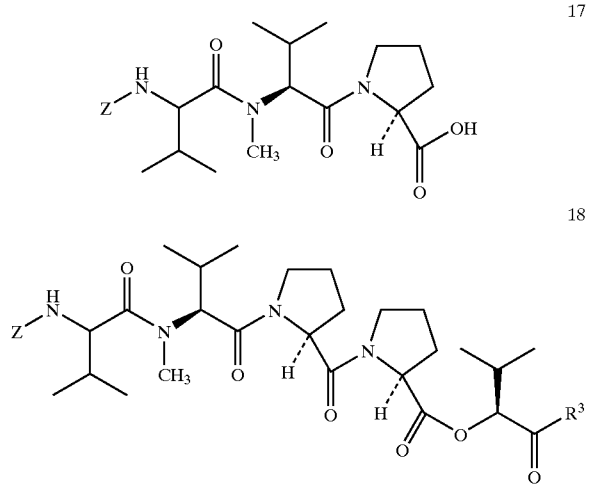

wherein Z is carboxybenzyloxy;

(e) removing the carboxybenzyloxy group from the tetrapeptide of formula 18 to form a deprotected tetrapeptide, and reacting said deprotected tetrapeptide with N,N'-dimethylvaline for a time and under conditions effective to generate said dolastatin 15 derivative of formula 13; and (f) recovering said dolastatin 15 derivative of formula 13.

4. A method of synthesizing a dolastatin 15 derivative according to claim 3 wherein step (a) is conducted in the presence of 4-methylmorpholine (NMM) and diethylphosphorocyanidate (DEPC).

5. A method according to claim 3 wherein step (a) is conducted in the presence of 1-hydroxybenzotriazole (HOBt), 4-methylmorpholine (NMM) and N,N'-dicyclohexylcarbodiimde (DCC).

6. A method according to claim 3 wherein step (b) is conducted in the presence of N,N'-dicyclohexylcarbodiimnide (DCC) and 4-pyrrolidinopyridine.

7. A method according to claim 3 wherein step (b) is conducted in the presence of 1-ethyl-3(3-dimethylaminopropyl)carbodiimide hydrochloride (EDC-HCl) and 4-pyrrolidinopyridine.

8. A method according to claim 3 wherein step (d) is conducted in the presence of $Et_3N$ and diethylphosphorocyanidate (DEPC).

9. A method according to claim 3 wherein in step (e) the tetrapeptide of formula 18 is deprotected in a solution of a tetrapeptide of formula 18 in EtOAc to which 10% Pd/C catalyst is added.

10. A method according to claim 3 wherein in step (e) the tetrapeptide of formula 18 is deprotected in a solution of a tetrapeptide of formula 18 in $CH_2Cl_2$ to which 10% Pd/C catalyst is added.

11. A method according to claim 3 wherein in step (e) the tetrapeptide of formula 18 is deprotected in the presence of a solution of a tetrapeptide of formula 18 suspended in glacial acetic acid to which 33% HBr/AcOH is added.

12. A method according to claim 3 wherein in step (e) the reaction of the tetrapeptide of formula 18 with N,N'-dimethylvaline is conducted in the presence of $Et_3N$ and diethylphosphorocyanidate (DEPC).

13. A method of synthesizing a dolastatin 15 derivative of formula 13

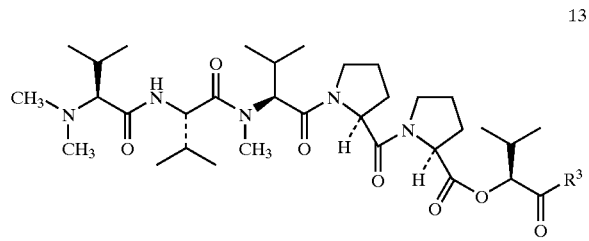

13 wherein $R^3$ is selected from the group consisting of:

NHPh, $NHCH_2Ph$, $NH(CH_2)_2Ph$, $NH(CH_2)_2$-4-F-Ph, $NH(CH_2)_2$-4-Cl-Ph, $NH(CH_2)_2$-3-Cl-Ph, $NH(CH_2)_2$-2-Cl-Ph, $NH(CH_2)_2$-4Br-Ph, $NH(CH_2)_2$-4-$NO_2$-Ph, $NH(CH_2)_2$-3,4-$(CH_3O)_2$Ph, $NH(CH_2)_2$-2-pyridine, $NH(CH_2)_3$-Ph, L-Phe-$OCH_3$, L-Met-$OCH_3$, L-Pro-$OCH_3$, NH-2-thiazolyl, NH-2-benzothiazolyl, and NH-3-quinolyl;

said method comprising:

(a) reacting 2-hydroxyisovaleric acid with an amine of formula $R^3$-H for a time and under conditions effective to form an amide of formula 14

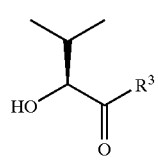

14 wherein R³ is as defined above;
(b) reacting the amide of formula 14 with tBoc-L-proline for a time and under conditions effective to form an ester of formula 15

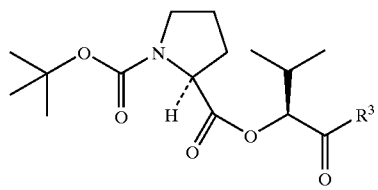

15

(c) treating the ester of formula 15 with trifluoroacetic acid for a time and under conditions effective to remove the tBoc group from the ester of formula 15, thereby generating a trifluoroacetic acid salt of formula 16

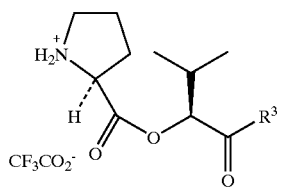

16

(d) reacting the trifluoroacetic acid salt of formula 16 with the tripeptide of formula 17 for a time and under conditions effective to generate the tetrapeptide of formula 18

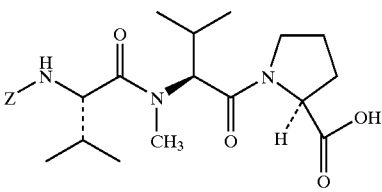

17

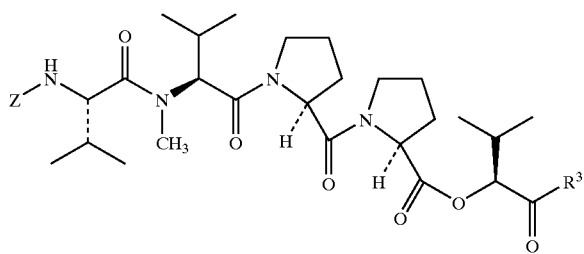

18 wherein Z is tBoc;
(e) removing the tBoc group from the tetrapeptide of formula 18 to form a deprotected tetrapeptide, and reacting said deprotected tetrapeptide with N,N'-dimethylvaline for a time and under conditions effective to generate said dolastatin 15 derivative of formula 13; and
(f) recovering said dolastatin 15 derivative of formula 13.

14. A method of synthesizing a dolastatin 15 derivative according to claim 13 wherein step (a) is conducted in the presence of 4-methylmorpholine (NMM) and diethylphosphorocyanidate (DEPC).

15. A method according to claim 13 wherein step (a) is conducted in the presence of 1-hydroxybenzotriazole (HOBt), 4-methylmorpholine (NMM) and N,N'-dicyclohexylcarbodiimide (DCC).

16. A method according to claim 13 wherein step (b) is conducted in the presence of N,N'-dicyclohexylcarbodiimide (DCC) and 4-pyrrolidinopyridine.

17. A method according to claim 13 wherein step (b) is conducted in the presence of 1-ethyl-3(3-dimethylaminopropyl)carbodiimide hydrochloride (EDC-HCl) and 4-pyrrolidinopyridine.

18. A method according to claim 13 wherein step (d) is conducted in the presence of Et₃N and diethylphosphorocyanidate (DEPC).

19. A method according to claim 13 wherein in step (e) the tetrapeptide of formula 18 is deprotected in the presence of a solution of a tetrapeptide of formula 18 in EtOAc to which 10% Pd/C catalyst is added.

20. A method according to claim 13 wherein in step (e) the tetrapeptide of formula 18 is deprotected in the presence of a solution of a tetrapeptide of formula 18 in CH₂Cl₂ to which 10% Pd/C catalyst is added.

21. A method according to claim 13 wherein in step (e) the tetrapeptide of formula 18 is deprotected in the presence of a solution of a tetrapeptide of formula 18 suspended in glacial acetic acid to which 33% HBr/AcOH is added.

22. A method according to claim 13 wherein in step (e) the reaction of the tetrapeptide of formula 18 with N,N'-dimethylvaline is conducted in the presence of Et₃N and diethylphosphorocyanidate (DEPC).

* * * * *